United States Patent
Crawley et al.

[11] Patent Number: 5,948,707
[45] Date of Patent: Sep. 7, 1999

[54] NON-SLIP, WATERPROOF, WATER VAPOR PERMEABLE FABRIC

[75] Inventors: Jerald M. Crawley; Michael A. Schmieder, both of Flagstaff, Ariz.; Craig D. Lack, Wilmington, Del.

[73] Assignee: Gore Enterprise Holdings, Inc., Newark, Del.

[21] Appl. No.: 09/041,364

[22] Filed: Mar. 9, 1998

[51] Int. Cl.⁶ ........................................................ B32B 7/14
[52] U.S. Cl. ........................... 442/101; 442/289; 442/397; 442/76; 428/422; 428/913
[58] Field of Search .................... 442/101, 289, 442/397, 76; 428/422, 913; 156/278, 305

[56] References Cited

U.S. PATENT DOCUMENTS

| | | |
|---|---|---|
| 3,953,566 | 4/1976 | Gore . |
| 3,978,259 | 8/1976 | Hilton ................................. 442/101 X |
| 4,098,268 | 7/1978 | Scott . |
| 4,194,041 | 3/1980 | Gore et al. . |
| 4,443,511 | 4/1984 | Worden et al. . |
| 4,464,431 | 8/1984 | Hisaki et al. ............................ 442/101 |
| 4,692,369 | 9/1987 | Nomi . |
| 4,925,732 | 5/1990 | Driskill et al. . |
| 4,989,593 | 2/1991 | Campagna et al. . |
| 5,016,622 | 5/1991 | Norvell . |
| 5,026,591 | 6/1991 | Henn et al. . |
| 5,061,555 | 10/1991 | Edenbaum et al. ...................... 442/101 |
| 5,102,711 | 4/1992 | Keller et al. . |
| 5,180,632 | 1/1993 | Edenbaum et al. ...................... 442/101 |
| 5,397,628 | 3/1995 | Crawley et al. . |

FOREIGN PATENT DOCUMENTS

| | | |
|---|---|---|
| 465 817 | 1/1992 | European Pat. Off. . |
| 2633844 | 2/1978 | Germany . |
| 79013560 | 5/1979 | Japan . |

*Primary Examiner*—Daniel Zirker
*Attorney, Agent, or Firm*—Wayne D House

[57] ABSTRACT

A non-slip, waterproof, water vapor permeable fabric and method of making are described. The fabric is made by obtaining a waterproof, water vapor permeable film and adhering one side of the film to a layer of fabric which may be a stretch fabric. The other side of the film is provided with a discontinuous coating of an elastomer which has an elastic modulus of less than $5.5 N/mm^2$. The discontinuous coating may take various forms including a pattern of dots or a grid of intersecting lines. The discontinuous coating may optionally project above the surface of the film. The presence of the discontinuous coating of elastomer results in a fabric with a static coefficient of friction of greater than about 1.0 on the discontinuously coated side of the fabric. The film is preferably a porous expanded polytetrafluoroethylene film provided with a hydrophilic coating on one surface; the hydrophilic coating may serve as an adhesive for joining the one surface of the film to the layer of fabric. The inventive fabric is useful for various applications such as articles of medical protective clothing including surgical drapes and liners for orthotic braces, which applications may benefit from the non-slip character of the fabric.

33 Claims, 2 Drawing Sheets

NON-SLIP, WATERPROOF, WATER VAPOR PERMEABLE FABRIC

FIELD OF THE INVENTION

The present invention relates to a non-slip, waterproof, water vapor permeable fabric material.

BACKGROUND OF THE INVENTION

Waterproof, breathable fabrics, that is, fabrics which are simultaneously water vapor permeable and water impermeable, are well known in the art. Garments of many different types are made from such fabrics. Some of these garments are intended for use over other fabrics while others are sometimes used in direct contact with the skin of a wearer. For most such applications it is desirable for the fabric to be able to move or slip with respect to the underlying skin or fabric layer with which it is in contact.

For other applications, however, a non-slip quality in such a waterproof, breathable fabric is appropriate. These applications include various garments such as socks and gloves, and medical protective clothing and articles such as surgical drapes and gowns, nursing pads and liners for orthotic devices such as casts and braces. A description of cast and brace liner applications is exemplary of the need for waterproof, breathable non-slip fabrics and the lack of suitable fabrics in the prior art to fulfill these needs.

Various orthopedic and orthotic devices and braces are commonly used to reinforce or immobilize a portion of the body of the wearer, usually a limb or joint. Casts are commonly employed when treating a bone fracture. In applying a conventional plaster cast, it is common practice to first cover the body member being treated with a protective fabric sleeve made of a material such as cotton or polyester knit fabric. The protective cloth-covered body member is then covered with cotton or polyester padding to provide a soft, resilient padded lining. The padding is then overwrapped with plaster and woven cloth wrapping applied to a thickness to provide an immobilizing cast about the limb.

It is also known to fabricate casts from fiberglass material in the form of flexible coated fiberglass fabrics which are wrapped about the body member and thereafter hardened by cooling or by application of energy such as ultra violet energy.

Similarly, it is known to apply various braces and orthotic devices to the body of the wearer, mainly to the limbs and joints. In some applications, these braces are compression members and in others include a compression member and some type of range of motion limiting device. Such devices are widely used in therapeutic applications and are also widely used in connection with athletic activities, particularly to protect joints such as the knee joints from injury.

Use of orthopedic casts, orthotic devices and braces in this manner often causes discomfort to the wearer. Conventional neoprene braces often cause an adverse allergic reaction resulting in skin irritation. These braces are also known to be excessively abrasive where they contact the skin and are likewise known to migrate from their desired placement during activity. The combination of their abrasive character and the migration frequently results in skin irritation and maceration. Perspiration coupled with a lack of circulation also allows irritation and maceration of the skin under the cast, device or brace which may result in the growth of bacteria and skin erosion. If untreated, this condition can lead to infection.

The following patents and product literature are representative of the prior art in the field of waterproof, breathable fabrics, non-slip fabrics and cast and brace liners which incorporate padding materials which may utilize such fabrics.

U.S. Pat. No. 4,194,041, commonly assigned herewith, describes a waterproof and breathable polytetrafluoroethylene (hereinafter PTFE) laminate which possesses high water vapor transmission even under adverse climatic conditions. Such laminates in modified forms are commercially available from W. L. Gore & Associates. The waterproof and breathable laminate described in this patent consists of a flexible outer layer of microporous hydrophobic material (such as porous, expanded PTFE, hereinafter ePTFE) having a moisture vapor or water vapor transmission rate (hereinafter WVTR) exceeding 1,000 $gms/m^2/day$ and an advancing water contact angle exceeding 90 degrees and a second interior layer of continuous hydrophilic elastomeric material attached to the interface of the outer layer. The interior layer has a water vapor transmission rate exceeding 1,000 $gms/m^2/day$ and does not permit the detectable passage of liquid water. The material is primarily for use in the fabrication of waterproof, breathable garments and the like.

U.S. Pat. No. 4,443,511, also commonly assigned, discloses a waterproof and breathable elastomeric PTFE layered article for use in protective articles. The waterproof and breathable layered article is formed by mechanically stretching a laminate composite article comprising a first layer of hydrophobic material (such as ePTFE) having a water vapor transmission rate exceeding 1,000 $gms/m^2/day$ and an elastomeric hydrophilic layer such as a polyether-polyurethane wherein a major portion of both layers are in continuous interlocking relationship with one another.

U.S. Pat. No. 4,692,369 describes a water vapor permeable, waterproof, highly elastic film. This film may be used in laminar form with various fabrics.

U.S. Pat. No. 4,989,593 discloses a rigid orthopedic cast or splint which includes a padding that is treated with a fluorochemical or silicone. The padding has a surface tension of less than 60 dynes per centimeter and a porosity of less than about 15 seconds. The padding is able to shed water rapidly, providing comfort to the user.

U.S. Pat. No. 5,016,622, commonly assigned herewith, discloses a orthopedic cast and padding assembly having a water impermeable water vapor permeable membrane in contact with the skin, a resilient padding layer, and a plaster or resin/glass fiber outer immobilizing layer. The assembly is said to increase the comfort of a wearer and reduce bacteria contained within the cast.

Another cast material is found in U.S. Pat. No. 5,102,711, also commonly assigned. This patent discloses a flexible, breathable, non-linting, composite having a middle layer of padding and a top and bottom layer comprising a sheet of water impermeable, water-vapor-permeable film bonded to the middle layer. Preferably the top and bottom layers comprise (a) a flexible first sheet of hydrophobic material having a water vapor transmission rate exceeding 1,000 $gms/m^2/day$; and (b) a continuous hydrophilic sheet attached to or penetrating the first sheet having a water vapor transmission rate exceeding 1,000 $gms/m^2/day$ and forming a barrier to passage of fluids. The composite material is useful in applications such as padding under orthopedic casts and thermal insulation in apparel. This material is available from W. L. Gore & Associates under the designation "Gore Cast Liner" and is more particularly shown in brochure no. C:96-04 Revised 1/97, issued by W. L. Gore & Associates, Inc., Flagstaff, Ariz.

U.S. Pat. No. 5,397,628, also commonly assigned herewith, discloses a body protection material having an inner layer of ePTFE laminated to an outer layer of substantially air impermeable cellular rubber. This material is useful in such applications as wetsuits or orthopedic braces, offering improved wearing comfort and reduced allergenic reactions in contrast to conventional cellular rubber body protection materials. Because the layers are laminated together, any tubular article made from the material is subject to migration during activity on the part of a wearer.

Product literature from Comfort Sleeves, Sacramento, Calif., describes a sleeve article intended for use with conventional braces. The article is made from polyolefin and cotton/Lycra materials and is stated to reduce bacterial growth and increase wearer comfort.

There is no indication that the article is waterproof.

Waterproof and water vapor permeable films and fabrics (including ePTFE films provided with elastomer coatings) have been provided previously with patterned coatings of other materials for various purposes. Specifically these include patterned coatings of adhesives to allow lamination to other surfaces and patterned coatings of harder materials (i.e., materials having an elastic modulus of greater than 5.5 $N/mm^2$ or 800 psi) intended to increase the abrasion resistance of ePTFE. Because of the use of relatively hard materials for these coatings, they do not provide non-slip properties to the ePTFE.

Thus, while there are various laminate and composite fabric materials available for use in applications where fabrics having vapor permeability and water impermeability are required, there nevertheless remains a need for such a material having non-slip properties for various diverse applications including cast and brace liners, socks gloves, surgical drapes and gowns, and nursing pads.

SUMMARY OF THE INVENTION

The present invention relates to a waterproof, water vapor permeable fabric material which has non-slip properties and to a method for making such material. The material comprises a waterproof, water vapor permeable film or membrane laminated to a layer of fabric. The film or membrane is preferably an ePTFE film. The opposite side of the film or membrane (the side away from the fabric layer) is provided with a discontinuous coating of an elastomeric material which provides the non-slip properties by substantially increasing the coefficient of friction of the film or membrane layer. The elastomeric material is adequately soft to provide the necessary increase in the coefficient of friction, having an elastic modulus of less than 5.5 $N/mm^2$. The resulting fabric has a static coefficient of friction of greater than 1.0, or greater than about 1.0, on the exposed film or membrane side which is generally the side facing a wearer.

In an alternative embodiment, the discontinuous coating of elastomer may be provided on the exterior surface of the fabric side of the film and fabric laminate, whereby this fabric surface also has a static coefficient of friction of greater than 1.0, or greater than about 1.0.

The discontinuous coating preferably forms projections above the surface of the film or membrane substrate, or alternatively the fabric substrate. It leaves a significant portion of the substrate surface uncoated by the elastomeric material. This uncoated portion of the inventive material therefore remains both waterproof and water vapor permeable. The coated portion of the inventive material may also be water vapor permeable to a lesser extent.

The discontinuous coating of elastomeric material on the surface of the film or membrane which results in the non-slip properties of the inventive material is the result of a surface treatment preferably applied to the film or membrane on the side opposing the fabric layer (the inner surface, e.g., the side of the membrane intended to contact or face toward the skin of a wearer). The surface treatment involves the application of the elastomeric material applied in a pattern, preferably a raised pattern, to that side of the membrane. Alternatively, as noted above, the dots may be applied to the outer surface of the fabric (opposite the film side). The pattern may be in the form of small domes or dots at spaced intervals or may be intersecting lines in various patterns such as a grid pattern applied to the one surface of the membrane or alternatively to the fabric surface. The pattern preferably comprises silicone dots applied by a screening or gravure process prior to forming the layered or laminate assembly.

The film or membrane is preferably a hydrophobic film layer having a water vapor transmission rate exceeding 1,000 gms/$m^2$/day. The WVTR of the inventive fabric must be greater than this value in order to be considered water vapor permeable. The waterproof character of the fabric is determined by a test for water resistance (Suter Test). One surface of the film or membrane is bonded to the fabric layer by an adhesive while the opposite surface forms the inner surface of the material(the surface intended to face toward a wearer). As noted above, the inner film layer is preferably ePTFE which has been found to prevent skin irritation and allergic reaction sometimes caused by prolonged contact between the skin and an adjacent surface. These ePTFE films or membranes are fabricated in accordance with the teachings of U.S. Pat. Nos. 3,953,566 and 4,187,390. The expanded, porous PTFE film is provided on one surface with a coating of a water vapor permeable polymeric resin such as an elastomer containing urethane bonds, waterproof and permeable to passage of water vapor through its thickness. The coating, which is preferably a polyurethane, prevents the ePTFE film from wetting out by exposure to contaminants such as body oils and perspiration, thereby maintaining the waterproof, water vapor permeable character of the ePTFE film during use. The resulting coated film has a water vapor transmission rate exceeding 1,000 gms/$m^2$/day. Fabrics incorporating these ePTFE films are commercially available under the registered trademark GORE-TEX® sold by W. L. Gore & Associates, Inc., Newark Del.

The above described polyurethane coating may also serve as the adhesive which bonds the ePTFE layer to the fabric substrate. This is preferred in order to maximize the water vapor permeability of the inventive material. Alternatively, another adhesive layer may be used in addition to the polyurethane coating; these additional adhesives may be applied either continuously or discontinuously. Polyurethanes are also the preferred adhesive for bonding the fabric layer to the coated ePTFE film layer, however, other elastomeric adhesives such as silicones, acrylics, and rubber based adhesives may also be used.

For many of these applications the inventive material is preferably a stretch fabric. These are preferably formed by mechanically stretching a stretchable, elastic knitted fabric made from nylon, Dacron or other synthetic or natural fiber. The material commonly known as spandex is preferred. The stretched fabric is then bonded to the ePTFE film layer. Once the assembly has been fabricated and the adhesive has cured, the stretched outer layer is released. The inner layer of ePTFE film may assume a crepe-like appearance due to the relaxation of the outer layer.

The inventive material is useful for any application where the waterproof and breathable qualities are desired and there is a need for reduced slippage when the material is in contact with human skin, another fabric or any other surface. Particular applications incorporating the material of the present invention may include various garments such as socks and gloves, surgical fabrics or medical protective clothing such as surgical drapes, surgical gowns and containment gowns, hair-cutting drapes and various non-garment fabric applications including orthotic applications such as cast and brace liners. For use as a surgical gown, the garment may be made to have sleeves with everted cuffs such that the length of the sleeve has a non-slip coating against the skin of the wearer while the cuff provides the non-slip coating facing outwardly where it may be used to prevent slippage of a surgical glove overlapping the outward facing surface of the cuff.

For orthotic applications, the non-slip material of the present invention is preferably fabricated into a tubular sleeve or other similar shape for application about the limb of a patient for use beneath a brace or other orthopedic device or appliance. Such a sleeve device may be useful as a liner beneath a brace worn to prevent carpal tunnel syndrome. In use, the sleeve remains substantially immobile with respect to the underlying skin, while the brace material (typically neoprene) is able to move with respect to the sleeve. Movement of the sleeve such as typically occurs is thus not damaging to the skin because of the intervening sleeve made of the fabric material of the present invention. Further, the sleeve when incorporating an inner layer comprising ePTFE, produces minimal adverse reaction because of the inert chemical character of the PTFE as well as because of the lack of relative movement between the skin and sleeve due to the non-slip character of the material.

Still another application of the inventive fabric may be as a non-slip fabric for the surface of a wheel chair seat cushion. The effectiveness of such a cushion may be improved by providing it with water vapor permeability and by providing a non-slip surface which can inhibit a person such as a paraplegic from inadvertently slipping from the chair cushion as a result of perspiration rendering the cushion surface excessively slippery. For such an application the described discontinuous elastomeric coating may alternatively be applied to the fabric side of the material rather than to the ePTFE membrane side.

The above aspects and advantages of the present invention will be more fully appreciated from the following description, claims and drawings.

DETAILED DESCRIPTION OF THE INVENTION

Figure 1:
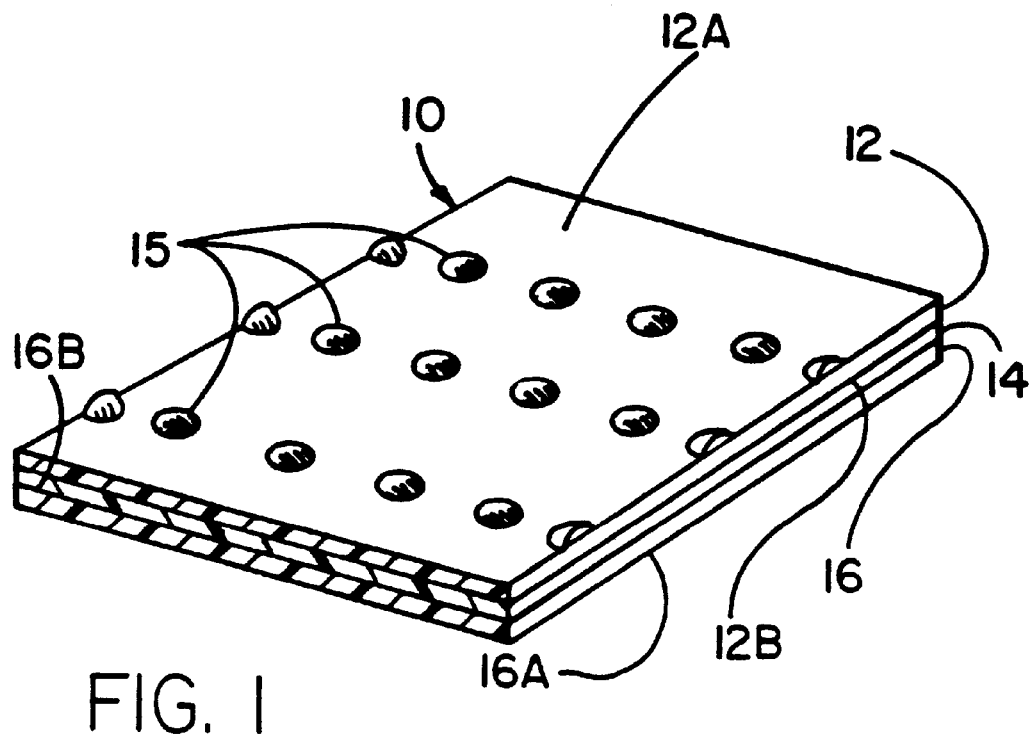
FIG. 1 is an enlarged perspective view, partly in cross section, of the material of the present invention showing the inner layer of ePTFE adhered to the outer layer of the fabric material with a layer of adhesive therebetween, and the discontinuous layer of elastomer applied to the surface of the ePTFE layer opposite the fabric layer.

FIG. 1 shows an enlarged perspective view which also illustrates in cross-section the fabric material of the present invention which is generally designated by reference number 10. The fabric material is a layered structure having an inner layer of a film or membrane 12 preferably of ePTFE with a suitable adhesive 14 applied over its unexposed surface 12B; adhesive 14 joins surface 12B of the inner film layer 12 to an inner surface 16B of layer of fabric 16. Outer surface 16A of fabric 16 becomes the outer surface of the inventive material, typically intended to face outwardly away from the skin of a wearer. Exposed surface 12A of film layer 12 is typically intended to be in direct contact with the skin of a wearer.

As used herein, the term "porous, expanded polytetrafluoroethylene," or "ePTFE," refers to a material formulated as disclosed in U.S. Pat. Nos. 3,953,566 and 4,187,390, both of which are incorporated by reference herein. The ePTFE films are inherently hydrophobic and resist entry and passage of liquid water while allowing passage of gases and water vapor through the films.

The adhesive 14 is preferably a polyurethane elastomer based adhesive or alternatively silicone elastomer which is flowed or otherwise applied to the surface 12B of film layer 12. The adhesive need only be applied in a thin layer, such as about 0.02 mm thickness. The adhesive interpenetrates the void spaces of the surface of the ePTFE to which it is applied as well as the void spaces of the fabric substrate, thereby ensuring effective bonding between the two. In use, the opposing surface 12A of film layer 12 is exposed and will be in contact with the skin surface of the wearer.

The ePTFE is also provided with a coating of polyurethane on one surface to render it liquid water impermeable and water vapor permeable as taught by U.S. Pat. No. 4,194,041, also incorporated by reference herein. The coating solution may be provided on either surface 12A or 12B of the ePTFE and as noted previously, assists by preventing the microporous ePTFE layer from becoming wetted by contaminants such as body oils or perspiration. Most preferably, this coating is applied to surface 12B of ePTFE layer 12 and also serves as adhesive layer 14 for adhering to fabric layer 16. The use of a combined coating solution and adhesive maximizes the water vapor permeability of the inventive material.

The outer fabric layer 16 is preferably a stretch fabric of the type of fabric known as spandex.

According to the *Encyclopedia of Textiles*, 3rd Edition, pages 310 to 315, there are two categories of stretch fabrics based on the degree of stretchability.

Power stretch fabrics have a higher degree of extensibility and quick recovery. Stretch factors generally range from 30% to 50% and with no more than 5% to 6% loss in recovery. Comfort stretch fabric is a term that applies to fabrics with less than 30% stretch factors. Such fabrics are widely used in athletic clothes such as exercise garments. It is preferred that the stretch material be considered a power stretch fabric for best results.

U.S. Pat. Nos. 4,443,511 and 4,692,369 describe laminates of ePTFE films and stretch fabrics which may be useful as precursor materials for the present invention.

Figure 2:
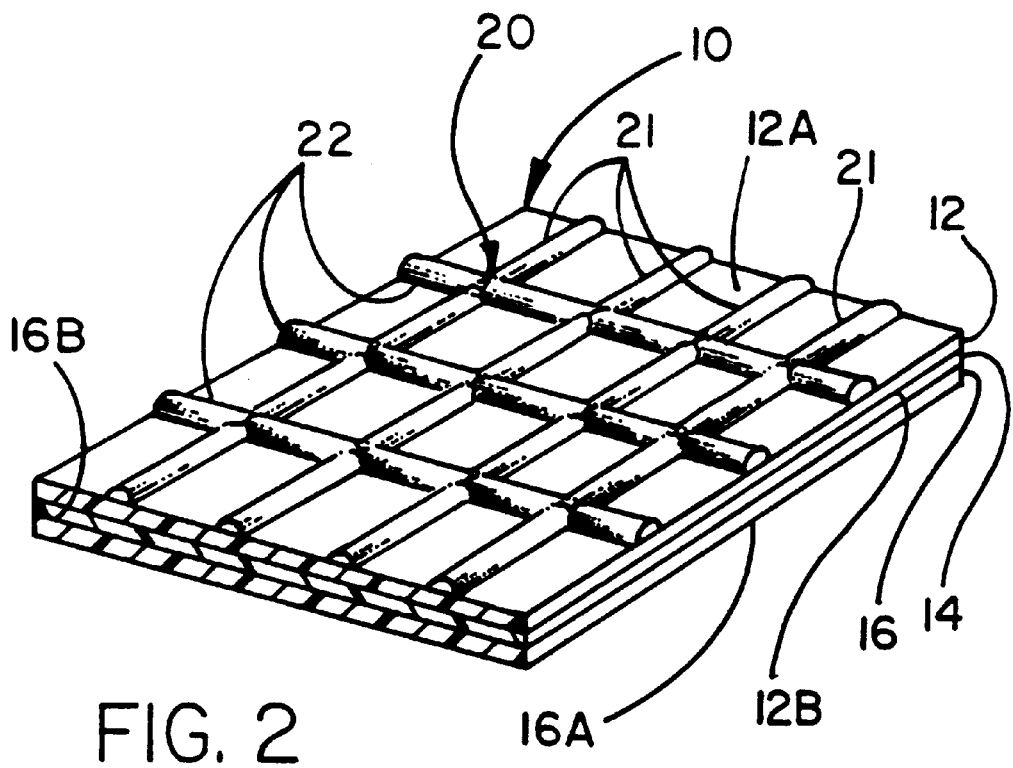
FIG. 2 is a perspective view similar to FIG. 2 showing an alternate form of surface treatment of the ePTFE film in which the surface has a grid-like pattern of elastomer thereon.

In order to minimize any movement of the ePTFE surface 12A with respect to a skin or other fabric surface with which it is in contact during use, at least a portion of the surface 12A of the ePTFE film 12 must be provided with a surface treatment which increases the coefficient of friction of surface 12A. As seen in FIGS. 1 and 2, the surface treatment comprises the application of an elastomeric material in a discontinuous pattern to surface 12A which pattern preferably comprises a plurality of small dot-like or dome-like projections 15. These dome-like structures are created by application of silicone, polyurethane or other elastomeric material which may be applied by spraying, screen printing or by a gravure process. The projections are applied in a discontinuous pattern extending across only a portion of the surface area of surface 12A, preferably having a size and distribution appropriate to cover between at least five percent and ninety percent of surface 12A of the film 12. More preferably, the pattern covers about 20–50 percent of the area of surface 12A. The patterns are discontinuous in the sense that they include open areas free of elastomeric material projecting upward from surface 12A.

The pattern of dots 15 may be a random pattern or an orderly pattern as desired for a specific application. The dots 15 need not be substantially hemispherical in shape as described by FIGS. 1 and 2, rather they may be of any desired shape including shapes such as generally described as squares, rectangles, polygons, etc. Shapes having a pointed or sharp tip, peak or ridge may also be used for specific applications.

The pattern selected for the application of the elastomeric material may intentionally be directionally asymmetric in order to provide for different coefficients of friction in different directions (e.g., directions parallel to the plane of the material and perpendicular to each other). This condition may be particularly desirable for certain applications (e.g., socks) which might benefit from increased resistance to slippage in one direction while allowing a greater amount of slippage in another direction.

For the necessary degree of non-slip performance, it is required that the elastomeric material used for the non-slip pattern have an elastic modulus of less than 5.5 N/mm$^2$ (800 psi). The elastic modulus of the elastomer may also be less than 5.0, 4.0, 3.0 or 2.0 N/mm$^2$. It is imperative that the elastomeric material chosen be adequately soft to provide the necessary gripping capability as used in contact with skin or another fabric surface. Typically, if the non-slip application involves contact with another fabric rather than direct skin contact, an elastomer of lower elastic modulus will be necessary. The selection of elastomer and the type of application pattern of the elastomer as well as the percentage of area coverage will need to be determined experimentally for each specific application of the inventive material. The coefficient of friction of the non-slip surface of the inventive fabric material was evaluated according to ASTM D 1894, Standard Test Method for Static and Kinetic Coefficients of Friction of Plastic Film and Sheeting, using a Monitor/Slip and Friction, Model 32-06 test apparatus manufactured by Testing Machines, Inc., Amityville, N.Y. All measurements were made using a 6.25 cm by 6.25 cm (2.5 inch by 2.5 inch) square sled of 200 g weight. Coefficient of friction data reported herein are the result of friction measurements made according to this ASTM Test Method between the described test specimen and a clean glass plate. The ePTFE film surface of the inventive material having the discontinuous coating of elastomer can be made in various forms having a static coefficient of friction of greater than about 1.0.

The phrase "non-slip" is used generally herein to describe a waterproof, water vapor permeable fabric having a surface which has been modified as described above resulting in substantially reduced slippage when used in contact against human skin or another fabric or other surface. The static coefficient of friction of this "non-slip" material is generally above about 1.0, 1.5, 1.7, 1.8, 1.9, 2.0, 2.1, 2.2, 2.3 and as high as 2.33 or higher, depending on the type of elastomer, the amount of the surface provided with the elastomeric covering and the type of pattern used.

In FIG. 2, a section of the film 12 is shown in which the surface treatment consists of a grid pattern 20 of intersecting grid lines 21 and 22 which again can be applied by any suitable process such as applying a silicone by screening, printing, spraying or flowing the surface treatment material onto the surfaces of the film 12 to create grid lines 21 and 22. The grid pattern shown is intended to be representative of many possible discontinuous patterns including, for example, zigzag lines.

Various elastomers may be useful as the discontinuous coatings in the form of different patterns with different spacings, etc. as described above. The various elastomers include silicones such as heat-cured silicones, condensation-cured silicones and RTV silicones. The elastomers may be applied by any of various methods which results in adequate bonding for the intended application. A preferred elastomer is RTV 863 from GE Silicones, Inc., Waterford, N.Y. This has been applied by gravure printing onto the desired surface of the substrate material and subsequently cured by heating appropriately. Exposure to a temperature of about 160 degrees C. for two minutes has been effective.

Figure 3:
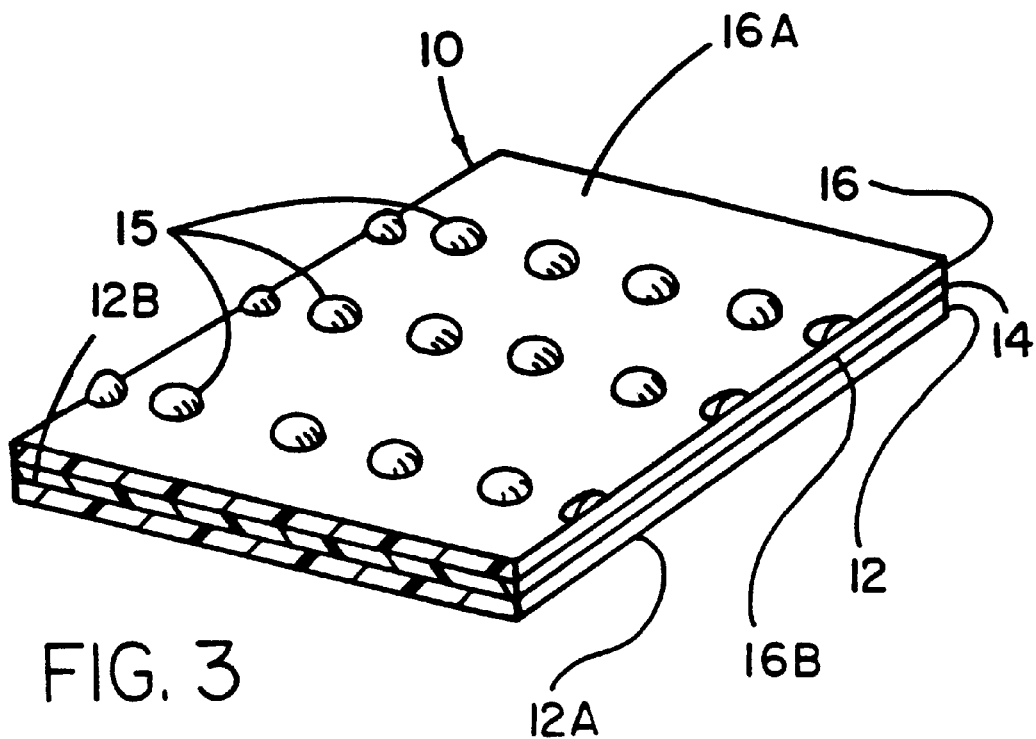
FIG. 3 is an enlarged perspective view, partly in cross section, of the an alternative embodiment of the material of the present invention showing the inner layer of ePTFE adhered to the outer layer of the fabric material with a layer of adhesive therebetween, and the discontinuous layer of elastomer applied to the surface of the fabric layer opposite the ePTFE layer.

FIG. 3 describes an enlarged perspective view, partly in cross section, of an alternative embodiment of the present invention showing the fabric material of the present invention having a discontinuous coating of elastomer applied to the fabric surface 16A rather than to the membrane surface 12A as described previously by FIG. 1. The coating may be applied by methods and patterns described herein and can provide the same static coefficient of friction values as the coating provided to the ePTFE membrane. This embodiment is anticipated to be useful for any applications where it may be advantageous for the waterproof, water vapor permeable material to have a fabric surface which has non-slip properties. One such application is anticipated to be as a non-slip fabric surface for a wheel chair cushion to reduce any tendency for a person being transported in a wheel chair to slide from the cushion surface during motion of the wheel chair. It is apparent that the described discontinuous coating of elastomer may be thus provided on either or both surfaces of the waterproof, water vapor permeable fabric depending on the demands of the intended application.

The waterproof and water vapor permeability qualities of the material may be tested by methods described herein. Water vapor permeability is evaluated by using the following test for water vapor transmission rate (WVTR) by the potassium acetate method.

Water Vapor Transmission Rate (WVTR) Test
(potassium acetate method)

Water Vapor Transmission Rate (WVTR), i.e. water-vapor-permeability, is measured by placing approximately 70 ml of a solution consisting of 35 parts by weight of potassium acetate and 15 parts by weight of distilled water into a 133 ml. polypropylene cup having an inside diameter of 6.5 cm at its mouth. An ePTFE membrane having a minimum WVTR of approximately 85,000 g/m$^2$/day (as tested by the method described in U.S. Pat. No. 4,862,730 to Crosby) is heat sealed to the lip of the cup to create a taut, leakproof, microporous barrier containing the solution.

A similar ePTFE membrane was mounted to the surface of a water bath. The water bath assembly was controlled at 23° C.±0.2° C., utilizing a temperature controlled room and a water circulating bath. The sample to be tested was allowed to condition at a temperature of 23° C. and a relative humidity of 50% prior to performing the test procedure. Three samples were placed so that each sample to be tested was in contact with the expanded PTFE membrane mounted over the surface of the water bath, and was allowed to equilibrate for at least 15 minutes prior to the introduction of the cup assembly.

The cup assembly was weighed to the nearest 1/1000 g and was inverted onto the center of the text sample.

Water transport was provided by the driving force between the water in the water bath and the saturated salt solution providing water flux by diffusion in that direction. The sample was tested for 20 minutes and the cup assembly was then removed and weighed again to within 0.001 g.

The WVTR of the sample was calculated from the weight gain of the cup assembly and was expressed in grams of water per square meter of sample surface area per 24 hours.

Water proofness is determined according to the test for water-resistance, or Suter Test as follows.

Suter Test

Samples of the present invention may be tested for water-resistance using a modified Suter test apparatus, which is a low water entry pressure challenge. The test procedure is set out in BS3424, method 29 C. Water is forced against the underside of a sample of 11.25 cm diameter sealed by two circular rubber gaskets in a clamped arrangement. A sample having a substrate of ePTFE with a hydrophilic coating on one side is mounted with the hydrophilic coating downwards against the water, the ePTFE membrane being uppermost. It is important that a leakproof seal is formed by the clamp mechanism, gaskets and sample. In deformable samples, the sample is overlaid by a reinforcing scrim (e.g. an open non-woven fabric) clamped over the sample. The upper side of the sample is open to the atmosphere and visible to the operator. The water pressure on the underside of the sample is increased to 2 psi (0.14 kg/cm$^2$) by a pump connected to a water reservoir, as indicated by a pressure gauge and regulated by an in-line valve. The upper side of the sample is visually observed for a period of three minutes for the appearance of any water which might be forced through the sample in the event of lack of water-resistance. Liquid water seen on the surface is interpreted as a deficiency in the water-resistance of the sample (i.e., a leak). The sample has passed the test if no liquid water is visible on the upper side of the sample within the three minute test period.

The following examples describe exemplary fabrics according to the present invention and exemplary articles incorporating such fabrics. All of these exemplary materials are waterproof and water vapor permeable.

EXAMPLE 1

Figure 4:
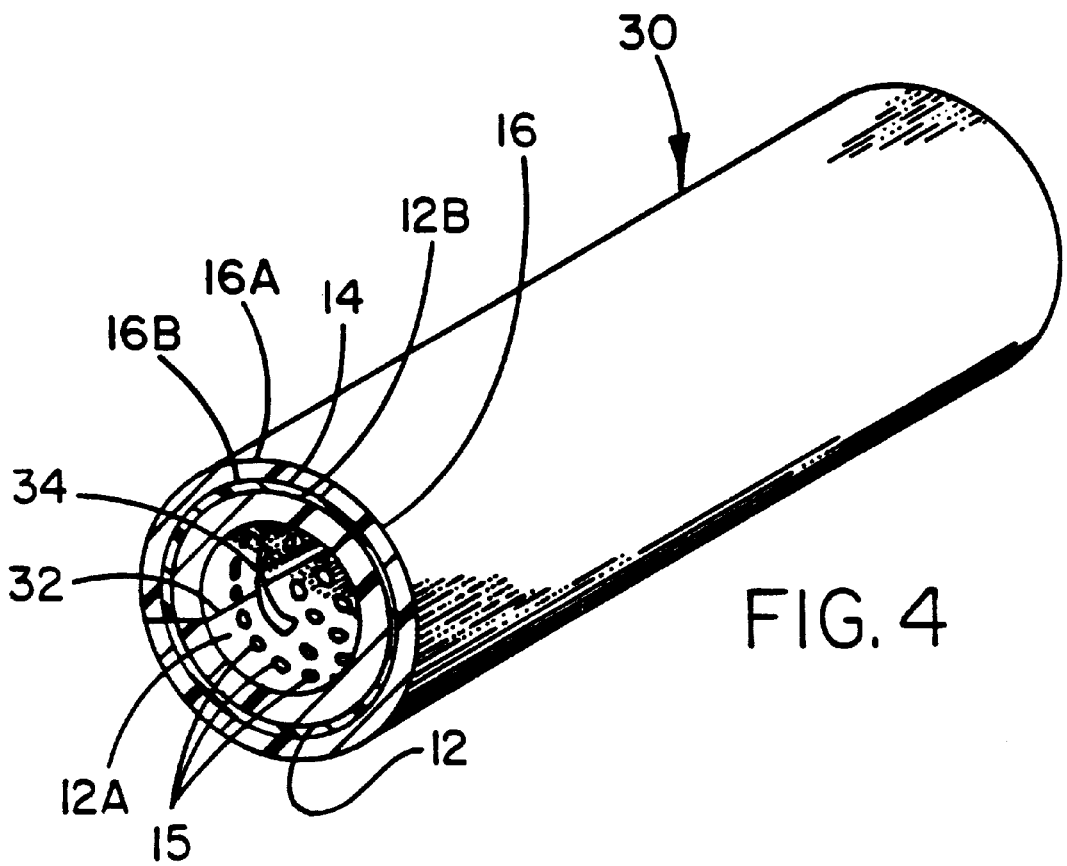
FIG. 4 is a perspective view of a tubular sleeve, useful as a braceliner formed from the non-slip material of the type shown in FIG. 1.

A two layer ePTFE stretch material (two layer clean room stretch material, PN 213740, W. L. Gore & Associates, Inc., Elkton, Md.) was used to make a tubular braceliner 30 as described with reference to FIG. 4. Briefly, this stretch material comprises an ePTFE film layer adhered to a layer of stretch fabric with a polyurethane coating solution as the adhesive.

The ePTFE side was provided with a discontinuous coating of an elastomer in the form of a dot pattern. Silicone elastomer (GE RTV 863, G.E. Silicones, Waterford, N.Y.) was used to create the dots which were applied by a gravure process. The dots were of about 1.84 mm diameter and arrayed in rows of dots in which the dots of adjacent rows were offset from each other with the result that the dots are arrayed in a triangular pattern as opposed to a square pattern. The distance between the edges of dots closest to each other was about 0.80 mm while the distance to the nearest edge of offset dots in the adjacent row was 1.20 mm. The dots appeared to be raised slightly above the surface of the ePTFE film when viewed by the naked eye. The discontinuously coated ePTFE film had a static coefficient of friction of 2.0. The stretch material was cut into a square sheet of about 32 cm length on each side. The direction of stretch for this sheet was oriented to provide the finished tubular braceliner with stretch in the radial direction. The seam 32, oriented in a direction substantially parallel to the longitudinal axis of the intended tubular form of the braceliner, was created by placing the material by hand into a Union Special Corp. sewing machine, Model No. 36200A (Union Special Corp., West Berlin, N.J.) and using four strands of Coats American TKT 60/36 cotton wrapped polyester core thread to form a flatlock stitch. The resulting tubular form 30 was moved to a Gore model 5000 seam sealing machine set to a sealer temperature of about 502 degrees C., a quill pressure of about 560 KPa, an air pressure of about 70 KPa and a feed rate of 2.4 m/min. The tubular form 30 was turned inside out, gathered up and placed around the feed roller horn with the leading edge of the seam to be sealed placed on top on the feed roller. Next, the feed roller and clamping mechanism were engaged by actuating the foot switch. The tubular braceliner fed through the machine and the seam seal tape 34 (two layer HNA014GN, 7/8 in.(2.2 cm), W. L. Gore & Associates, Inc., Elkton, Md.) was applied over the seam, after which the tubular form 30 of the braceliner was again everted to orient it properly for wearing. Seam tape leaders before and after the seam were trimmed for an improved aesthetic appearance. For many applications, an important advantage of the water proof, water vapor permeable materials of the present invention is their ability to be seam-sealed.

Braceliners made as described above were worn with knee braces by three individuals during light to moderate activities which included jogging and upper body weight lifting. Each individual wore a pair of knee braces, one with the inventive braceliner beneath it and the other without the braceliner as a control. The braceliner was always worn with the elastomeric dot patterned ePTFE against the skin. Two individuals used SafeTGard model no. 437 knee braces (Golden, Colo.) while the other wore a Stromgren Model no. 764 knee brace (Stromgren Supports, Inc., Hayes, Kans.). Wearing times ranged from 45 minutes to two hours. These users reported no hair pulling during the process of putting on and subsequently removing the brace with the inventive liner, while putting on and removing the control brace resulted in noticeable hair pulling. Wearers reported that the control brace resulted in the generation of a greater amount of heat and sweat than did the brace with the inventive braceliner. The control brace also was more likely to move out of place and require adjustment of its position than the brace with the liner, and also more likely to cause pinching during wearing. Finally, the control brace was reported to feel more abrasive and simply less comfortable overall.

EXAMPLE 2

Various samples of ePTFE film and fabric laminates were made in order to evaluate the coefficient of friction of such materials which might be used for different applications such as surgical drapes. These samples are described in Table 1 and were made using different patterns of discontinuous coatings as noted in the table. All fabric samples were laminated to the same ePTFE membrane material. The control sample was laminated to a Nylon woven fabric for which the coefficients of friction were determined for the ePTFE side which did not have a discontinuous elastomeric coating. Inventive samples (particularly the non-stretch laminates) were deemed to have potential use as surgical drape and gown materials. The stretch laminate material referred to in the table as having the large dot coating is the same fabric used for the braceliner of Example 1. The small dot coating differs in that the dots are of 0.53 mm diameter with a distance of 0.19 mm between the closest edges of adjacent dots and 0.30 mm from the nearest edges of the offset dots of the adjacent row. The fine grid pattern (7.87 lines/cm or 20 lines/inch) used with the polyester woven material used a line width of 0.35 mm, while the coarse grid pattern (3.94 lines/cm or 10 lines/inch) used a line width of 0.40 mm. In the case of all patterns used, the non-slip pattern appeared to rise slightly above the (surface of the ePTFE film when viewed by the naked eye. The elastomer used and method of application was the same as described for the large dots of Example 1.

| Sample | Non-Slip Surface | Non-Slip Surface Coverage (%) | Static Coefficient Of Friction | Kinetic Coefficient of Friction |
| --- | --- | --- | --- | --- |
| Control Nylon Woven | None | 0 | 0.66 | 0.57 |
| Nylon Woven | 3.94 lines/cm grid | 25% | 1.83 | 1.71 |
| Polyester Woven | 7.87 lines/cm grid | 49% | 2.33 | 2.14 |
| Nylon Woven | Small dots | 40% | 2.06 | 1.88 |
| Stretch Laminate | Small dots | 40% | 2.01 | 1.88 |
| Stretch Laminate | Large dots | 30% | 2.00 | 1.84 |

It will be appreciated from the foregoing that the present invention provides a material which is biocompatible and provides non-slip properties.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. A non-slip, waterproof, water vapor permeable material comprising a film of porous expanded polytetrafluoroethylene having first and second opposing surfaces, wherein said first surface is provided with a discontinuous coating of an elastomer and said first surface with the discontinuous coating of the elastomer has a static coefficient of friction greater than about 1.0, and wherein said second surface is adhered to a layer of fabric.

2. A non-slip, waterproof, water vapor permeable material according to claim 1 wherein said first surface has a static coefficient of friction greater than about 1.5.

3. A non-slip, waterproof, water vapor permeable material according to claim 1 wherein said first surface has a static coefficient of friction greater than about 1.8.

4. A non-slip, waterproof, water vapor permeable material according to claim 1 wherein said first surface has a static coefficient of friction greater than about 2.0.

5. A non-slip, waterproof, water vapor permeable material according to claim 1 wherein said first surface has a static coefficient of friction greater than about 2.3.

6. A non-slip, waterproof, water vapor permeable material according to claim 1 wherein said elastomer has an elastic modulus of less than 5.5 N/mm$^2$.

7. A non-slip, waterproof, water vapor permeable material according to claim 6 wherein said elastomer has an elastic modulus of less than 4.0 N/mm$^2$.

8. A non-slip, waterproof, water vapor permeable material according to claim 6 wherein said fabric is a stretch fabric.

9. A non-slip, waterproof, water vapor permeable material according to claim 8 wherein said stretch fabric is a sheet having two opposing edges which are joined to create a tubular form.

10. A non-slip, waterproof, water vapor permeable material according to claim 9 wherein said tubular form is a braceliner.

11. A non-slip, waterproof, water vapor permeable material according to claim 1 wherein said fabric is a stretch fabric.

12. A non-slip, waterproof, water vapor permeable material according to claim 11 wherein said stretch fabric is a sheet having two opposing edges which are joined to create a tubular form.

13. A non-slip, waterproof, water vapor permeable material according to claim 12 wherein said tubular form is a braceliner.

14. A non-slip, waterproof, water vapor permeable material according to claim 1 wherein said second opposing surface of said film is adhered to the layer of fabric by an adhesive selected from the group of adhesives consisting of silicone adhesives, polyurethane adhesives, acrylic adhesives and rubber based adhesives.

15. A non-slip, waterproof, water vapor permeable material according to claim 1 wherein said second opposing surface of said film is adhered to the layer of fabric by a polyurethane adhesive.

16. A non-slip, waterproof, water vapor permeable material according to claim 15 wherein said polyurethane adhesive is a polyether polyurethane.

17. A non-slip, waterproof, water vapor permeable material according to claim 1 wherein said discontinuous coating is a raised coating extending above the first opposing surface of the film.

18. A non-slip, waterproof, water vapor permeable material according to claim 1 wherein said discontinuous coating is a silicone coating.

19. A non-slip, waterproof, water vapor permeable material according to claim 1 wherein said discontinuous coating is a polyurethane coating.

20. A non-slip, waterproof, water vapor permeable material according to claim 1 wherein said discontinuous coating comprises a pattern of dots.

21. A non-slip, waterproof, water vapor permeable material according to claim 1 wherein said discontinuous coating comprises a pattern of lines.

22. A non-slip, waterproof, water vapor permeable material according to claim 1 wherein said pattern of lines comprises a grid pattern.

23. The non-slip, waterproof, water vapor permeable material according to claim 1 incorporated into an article of medical protective clothing.

24. A non-slip, waterproof, water vapor permeable material comprising a layer of fabric having first and second opposing surfaces wherein the first opposing surface is laminated to a layer of porous expanded polytetrafluoroethylene and the second opposing surface is provided with a discontinuous coating of an elastomer, wherein the second opposing surface of the fabric having the discontinuous coating of the elastomer has a static coefficient of friction greater than about 1.0.

25. A non-slip, waterproof, water vapor permeable material according to claim 24 wherein said first surface has a static coefficient of friction greater than about 1.5.

26. A non-slip, waterproof, water vapor permeable material according to claim 24 wherein said first surface has a static coefficient of friction greater than about 1.8.

27. A non-slip, waterproof, water vapor permeable material according to claim 24 wherein said first surface has a static coefficient of friction greater than about 2.0.

28. A non-slip, waterproof, water vapor permeable material according to claim 24 wherein said first surface has a static coefficient of friction greater than about 2.3.

29. A non-slip, waterproof, water vapor permeable material according to claim 24 wherein said elastomer has an elastic modulus of less than 5.5 N/mm$^2$.

30. A method of making a non-slip, waterproof, water vapor permeable material comprising:
   a) obtaining a porous expanded polytetrafluoroethylene film having first and second opposing sides;
   b) adhering a layer of fabric to the first opposing side of the porous expanded polytetrafluoroethylene film; and
   c) providing the second opposing side of the porous expanded polytetrafluoroethylene film with a discontinuous coating of an elastomer having an elastic modulus less than 5.5 N/mm2.

31. A method of making a non-slip, waterproof, water vapor permeable material comprising:
   a) obtaining a porous expanded polytetrafluoroethylene film having first and second opposing sides;
   b) adhering a layer of fabric to the first opposing side of the porous expanded polytetrafluoroethylene film; and
   c) providing the second opposing side of the porous expanded polytetrafluoroethylene film with a discontinuous coating of an elastomer;

wherein said second opposing side of the porous expanded polytetrafluoroethylene film with the discontinuous coating of elastomer has a static coefficient of friction of at least about 1.0.

32. A method of making a non-slip, waterproof, water vapor permeable material comprising:
   a) obtaining a layer of fabric having first and second opposing sides;
   b) adhering a porous expanded polytetrafluoroethylene film to the first opposing side of the layer of fabric; and
   c) providing the second opposing side of the layer of fabric with a discontinuous coating of an elastomer having an elastic modulus less than 5.5 N/mm$^2$.

33. A method of making a non-slip, waterproof, water vapor permeable material comprising:
   a) obtaining a layer of fabric having first and second opposing sides;
   b) adhering a porous expanded polytetrafluoroethylene film to the first opposing side of the layer of fabric; and
   c) providing the second opposing side of the layer of fabric with a discontinuous coating of an elastomer;

wherein said second opposing side of the layer of fabric with the discontinuous coating of elastomer has a static coefficient of friction of at least about 1.0.

* * * * *